United States Patent [19]

Fujiwara et al.

[11] Patent Number: 5,122,904
[45] Date of Patent: Jun. 16, 1992

[54] OPERATING MICROSCOPE WITH DRAPE AND SUCTION MEANS FOR REMOVING AIR FROM THE DRAPE

[75] Inventors: Hiroshi Fujiwara, Hachiouji; Masami Hamada, Setagaya; Shigeo Tokunaga, Hino; Masahiko Kinukawa, Higashimurayama; Tomonori Ishikawa; Takashi Fukaya, both of Hachiouji; Masanori Kaneda, Ina; Kenji Yoshino, Tama; Tadao Hagino, Yokohama, all of Japan

[73] Assignee: Olympus Optical Co., Ltd., Tokyo, Japan

[21] Appl. No.: 600,839

[22] Filed: Oct. 22, 1990

[30] Foreign Application Priority Data

Oct. 23, 1989 [JP] Japan .................. 1-275241
Aug. 8, 1990 [JP] Japan .................. 2-210066
Aug. 8, 1990 [JP] Japan .................. 2-210067

[51] Int. Cl.⁵ ............... B65D 85/38; B65D 65/02; G02B 21/00
[52] U.S. Cl. .................. 359/510; 206/316.1
[58] Field of Search ............. 350/585; 206/316.1

[56] References Cited

U.S. PATENT DOCUMENTS

| 3,528,720 | 9/1970 | Treace . | |
|---|---|---|---|
| 3,542,450 | 11/1970 | Terhune | 350/585 |
| 3,698,791 | 10/1972 | Walchle et al. . | |
| 3,796,477 | 3/1974 | Geraci . | |
| 4,045,118 | 8/1977 | Geraci . | |
| 4,183,613 | 1/1980 | Walchle et al. . | |
| 4,266,663 | 5/1981 | Geraci | 350/585 |
| 4,561,540 | 12/1985 | Hunter et al. | 350/585 |
| 4,799,779 | 1/1989 | Mesmer | 350/585 |

Primary Examiner—Jon W. Henry
Attorney, Agent, or Firm—Cushman, Darby & Cushman

[57] ABSTRACT

The operating microscope comprises at least one suction port formed in a microscope body or an arm for supporting the microscope body which is to be enveloped in a drape, and an exhaust fan or exhaust pump connected to the suction port. An exhaust port to be connected to an exhaust pump may be formed in the drape. Since air is exhausted out of the drape, and the drape is brought into close contact with the microscope body and the arm by operating the exhaust fan or the exhaust pump, the drape does not constitute a hindrance in the visual field of a surgeon or dgrade operability of the microscope.

9 Claims, 9 Drawing Sheets

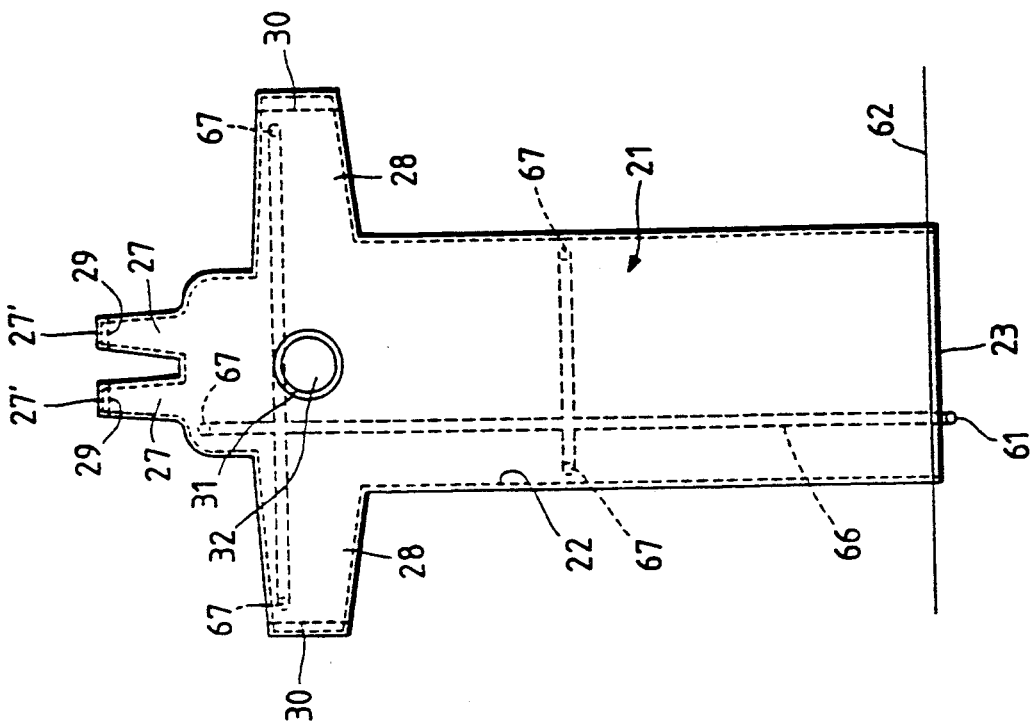
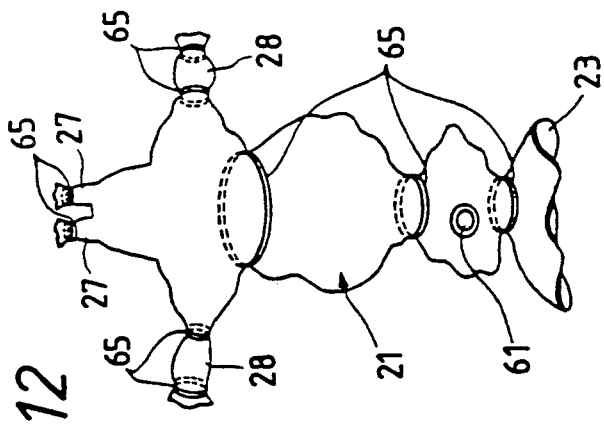
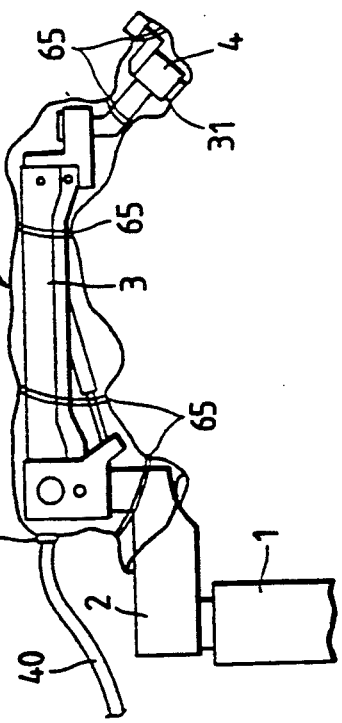

OPERATING MICROSCOPE WITH DRAPE AND SUCTION MEANS FOR REMOVING AIR FROM THE DRAPE

BACKGROUND OF THE INVENTION (a) Field of the Invention

The present invention relates to an operating microscope, and more specifically to an operating microscope which uses a drape.

(b) Description of the Prior Art

While the use of drapes is prevailing for enveloping operating, microscopes therein so as to maintain the exteriors thereof in a sterilized condition, it is conventional to fix the enveloping drapes to the microscope support arm or the similar members by bundling the drapes with rubber bands or strings.

However, the conventional fixing method allows the drapes to be slackened or swollen by heat emitted from lamps, etc. and, especially when the microscope bodies and arms are moved during surgical operations, the drapes are kept swollen at specific portions thereof by the air displaced by moving the microscope bodies and arms, thereby constituting hindrance in visual fields of surgeons. When the drapes are kept swollen, they may be cut open by scalpels which are accidentally brought into contact with the drapes, thereby making them incapable of maintaining the sterilized condition and constituting risks to patients. Further, tedious procedures are required to fix the drapes at numerous locations with strings or the similar means for removing the slacks and the drapes which are fixed at such numerous locations degrade operability of operating microscopes.

SUMMARY OF THE INVENTION

In view of the problems described above, it is a primary object of the present invention to provide a drape which is adapted to envelope a microscope body and an arm in a close contact condition as well as an operating microscope suited for use with said drape.

According to the present invention, this object is attained by forming at least one suction port in the microscope body or the microscope body support arm to be enveloped in the drape, or at least one exhaust port in the drape for exhausting air out of the drape. By placing an exhausting means connected to said suction port or the exhaust port during a surgical operation in the operating condition thereof, air is exhausted out of the drape and it is brought into close contact with the microscope body or the arm. Accordingly, the drape enveloping the operating microscope does not constitute a hindrance in the visual field of a surgeon nor degrade operability of the operating microscope.

This and other objects as well as the features and the advantages of the present invention will become apparent from the following detailed description of the preferred embodiments when taken in conjunction with the accompanying drawings.

BRIEF DESCRIPTION OF THE DRAWINGS

FIG. 12 is a perspective view illustrating still another example of the drape according to the present invention;

FIG. 13 is a side view illustrating the main parts of an Embodiment 4 of the operating microscope according to the present invention in a condition where it uses the drape shown in FIG. 12; and FIG. 14 through FIG. 16 are plan views illustrating other examples of the drape according to the present invention which are different from one another.

DESCRIPTION OF THE PREFERRED EMBODIMENTS

Figure 1:
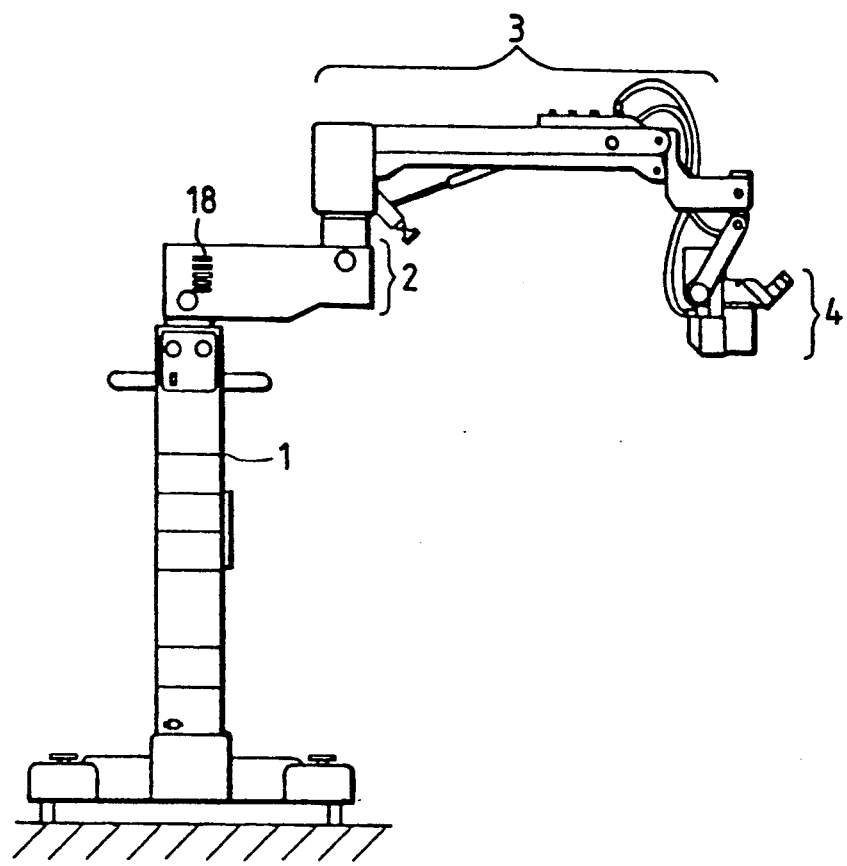
FIG. 1 is a side view illustrating an overall profile of an Embodiment 1 of the operating microscope according to the present invention.
Figure 3:
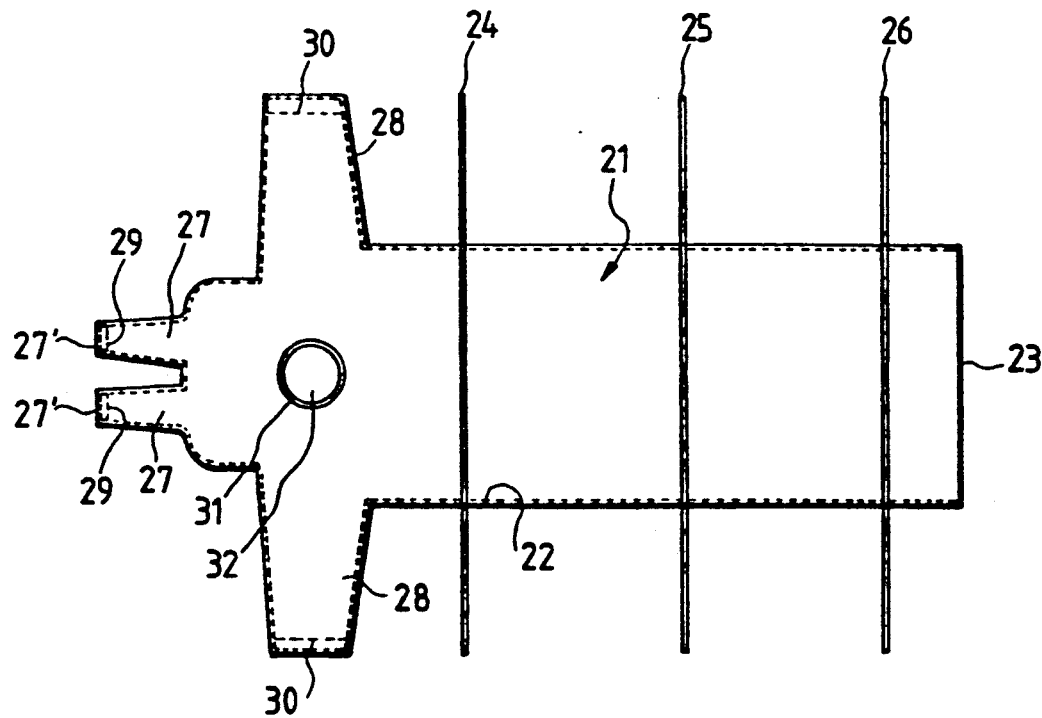
FIG. 3 is a plan view illustrating an -example of the drape according to the present invention.
Figure 2:
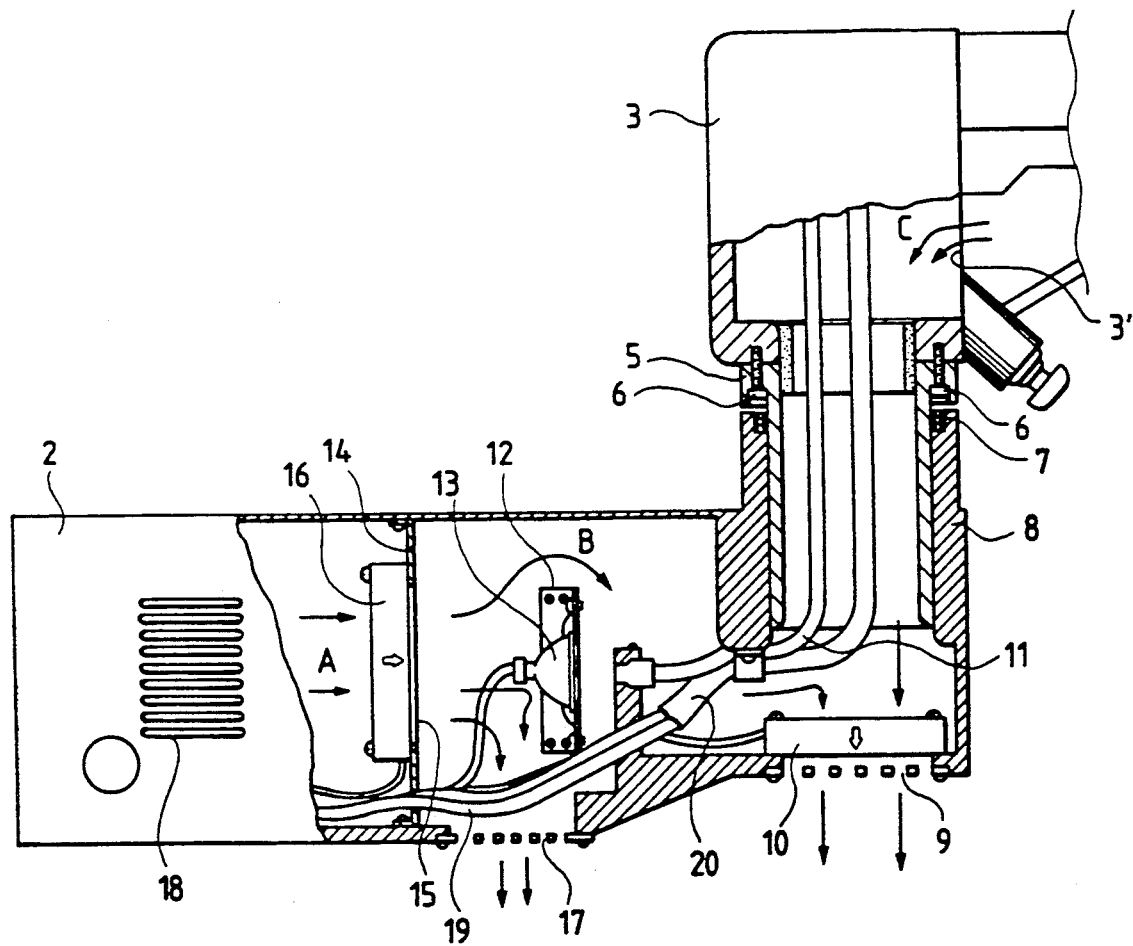
FIG. 2 is a side view partially exploded for illustating the main parts of the Embodiment 1 shown in FIG. 1 on a large scale.

Now, the Embodiment 1 of the present invention will be described below with reference to FIG. 1 through FIG. 4. In FIG. 1, the reference numeral 1 represents a stand, the reference numeral 2 designates a light source arm mounted on the stand 1 so as to be rotatable in the horizontal direction, the reference numeral 3 denotes a microscope body support arm mounted on the light source arm 2 so as to be movable in the vertical direction and rotatable in the horizontal direction, and the reference numeral 4 represents a microscope body sustained by the arm 3. FIG. 2 illustrates the connection between the light source arm 2 and the microscope body support arm as well as internal structure of the light source arm 2. In this drawing, the reference numeral 5 represents a cylindrical shaft which is attached to the arm 3 with bolts 6 and used for passing a cable and so on to be described later. By fitting this cylindrical shaft 5 into a cylinder 8 of the light source arm with ball bearings 7 interposed, the microscope body support arm 3 is mounted on the light source arm 2 in the condition where the former is rotatable in the horizontal direction. The reference numeral 9 designates vent holes formed in the bottom of the cylinder 8, the reference numeral 10 denotes a fan which composes an exhaust means in combination with the vent holes, the reference numeral 11 represents a light guide which has an end for light incidence fixed to a bracket arranged in the arm 2 and passes through the cylinder 8 into the microscope body support arm 3, the reference numeral 12 denotes a lamp mounting member fixed to the light source arm 2, the reference numeral 13 designates a lamp which is detachably mounted to the lamp mounting member in such a direction as to face the end of light incidence of the light guide 11, the reference numeral 14 represents a fan mounting member which is fixed to the light source arm 2 and has an opening 15, the reference numeral 16 designates a fan attached to the fan mounting member 14, the reference numeral 17 denotes vent holes formed under the lamp 13, the reference numeral 18 represents vent slots formed in the side wall of the light source arm 2, and the reference numeral 19 designates a cable which is used for transmitting driving signals from the stand 1 to a driving section in the microscope body 4, covered with a protective tube 20 over the section located within the cylindrical shaft 5 and fixed to the light source arm 2 together with the light guide 11 by using a cable clamp. The powers for operating the fan 10, fan 16 and lamp 13 are supplied from the stand 1. FIG. 3 shows a bag-like drape 21 fabricated from a very thin, flexible, clear sheet. In FIG. 3, the reference numeral 22 represents bonded edges of front and rear sheets, the reference numeral 23 designates an open end, the reference numerals 24, 25 and 26 denote strings which are welded to the drape 21 and to be used for binding the drape for preventing it from slackening, the reference numeral 27 represents eyepiece lens accommodating portions, the reference numeral 28 designates accessory accommodating portions to be used for attaching a side viewer, TV camera, etc. to the microscope body 4, the reference numerals 29 and 30 denote sewed lines for facilitating to remove or pull off the tips of the eyepiece lens accommodating portions 27 and the accessory accommodating portions 28, the reference numeral 31 represents an expansible objective lens cap, and the reference numeral 32 designates a clear plastic plate which is detachably fitted in the objective lens cap 32.

Figure 4:
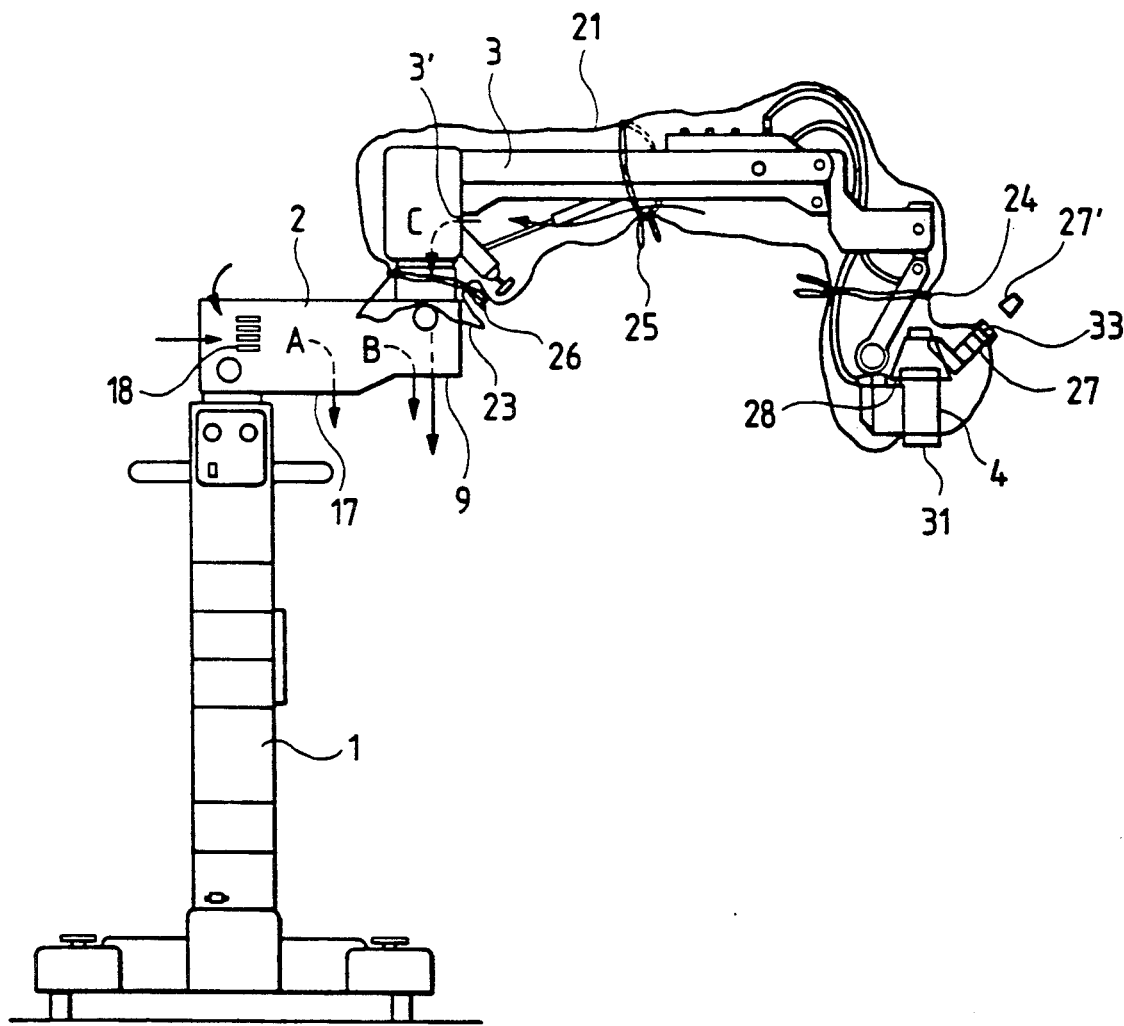
FIG. 4 is a side view, similar to FIG. 1 illustrating the overall profile of the Embodiment 1 in a condition wherein it uses the drape shown in FIG. 3.

Prior to description of the functions of the Embodiment 1 of the present invention, a description will be made of the procedures to envelop the operating microscope in the drape 21 with reference to FIG. 4. With the open end 23 kept spread, the drape 21 is fitted over the operating microscope so as to envelop the microscope body 4, the microscope body support arm 3 and the light source arm 2, the eyepiece tubes are fitted into the eyepiece accommodating portions 27 and 27 repectively, the ends of the eyepiece lens accommodating portions are fixed with rubber bands 33, and the tips 27' thereof are cut off along the sewed line 29 by pulling them. Then, the objective lens cap 31 is fitted over the objective lens, and finally the drape 21 is bound to the microscope body 4, microscope body support arm 3 and light source arm 2 repectively with the strings 24, 25 and 26 so that the drape 21 will not hinder surgical operation or degrade operability of the operating microscope. Accordingly, the mocroscope support arm 3, the microscope body 4 and the surroundings thereof are kept in a sterilized condition. At this stage, the accessory accommodating portions 28 are folded and fixed to the drape 21 with tapes or similar means and, when an accessory is to be used for microscopy, can be handled like the eyepiece lens accommodating portions 27. By operating the fans 10 and 16 after the drape 21 has been fitted as described above, ambient air is taken into the light source arm 2 through the vent holes 18, flows in the direction indicated by the arrows A, passes through the fan 16, strikes against the lamp mounting member 12. Most of the air flows outside through the vent holes 17, whereas rest portion flows as indicated by the arrow B. The fan 10 functions to flow out the air flow B sent by the fan 16 through the vent holes 9 and suck air from inside the drape 21 through the vent hole 3' (FIG. 2) formed in the microscope support arm 3 as indicated by the arrows C for exhausting the air outside also through the vent holes 9. Since the interior of the drape 21 is kept substantially in an airtight condition, internal pressure is lowered by exhausting air as described above, and the drape 21 is deflated and brought into close contact with the microscope body and the arm. Accordingly, the drape 21 constitutes nearly no hindrance in the visual field of a surgeon or degrade operability of the operating microscope and serves for efficient cooling of the lamp 13 in the light source arm 2. Further, the Embodiment 1 does not require any particular intake pump and can be realized inexpensively. Though the Embodiment 1 uses two fans for cooling the lamp by sucking and exhausting air, it is possible, when the lamp has a small heat capacity or a fan has high air exhaust capacity, to use a single fan for carrying out the cooling of the lamp as well as the suction and exhaust of air out of the drape at a lower cost.

Figure 5:
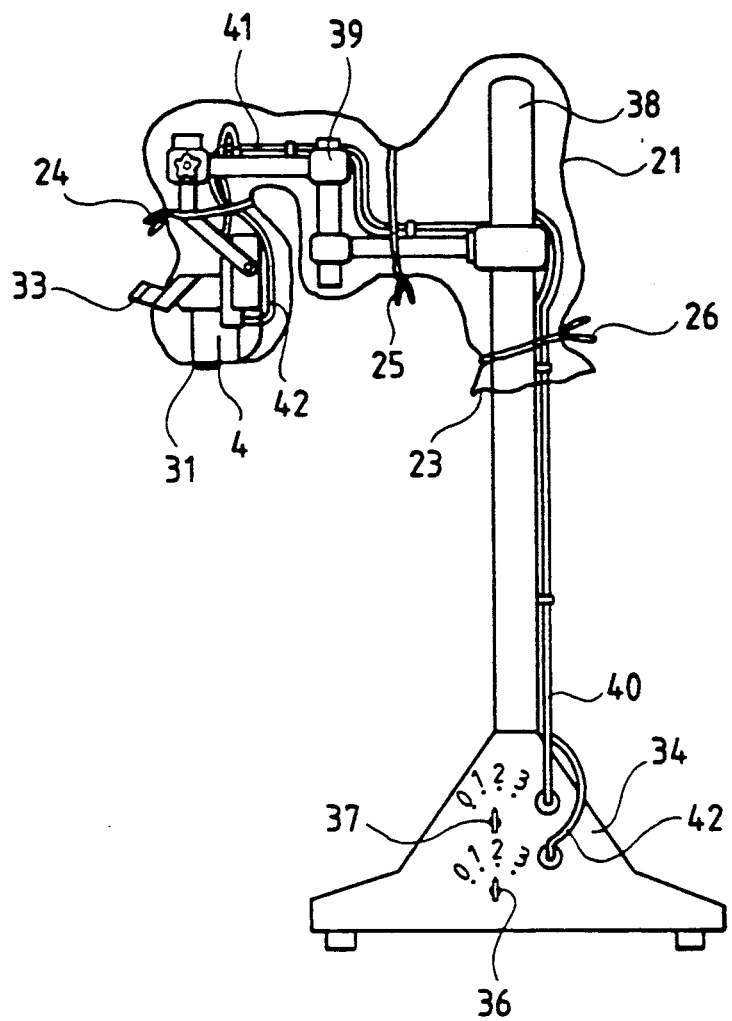
FIG. 5 is a side view illustrating an Embodiment 2 of the operating microscope according to the present invention in a condition where it uses the drape shown in FIG. 3.
Figure 6:
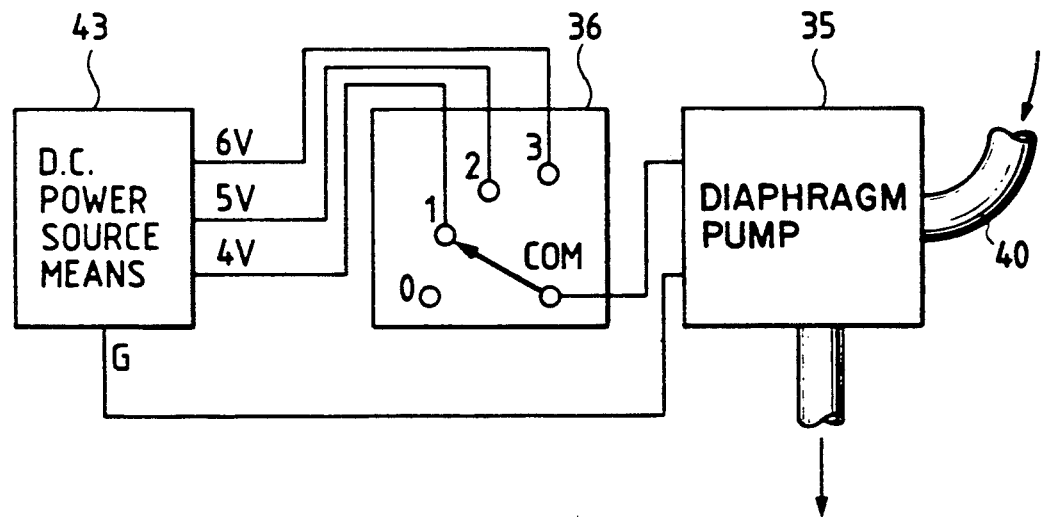
FIG. 6 is a diagram illustrating a power source circuit for a diaphragm pump to be used in the Embodiment 2 shown in FIG. 5.

FIG. 5 and FIG. 6 illustrate the Embodiment 2 of the invention. In the drawings, the members and parts which are the same as those used in the Embodiment 1 are represented by the same reference numerals. The reference numeral 34 denotes a stand which comprises a power source controller for focusing the microscope body 4 and varying magnification thereof as well as a diaphragm pump 35 to be described later, the reference numeral 36 designates a selector switch which is arranged on the stand 34 and used for varying brightness of illumination light by selecting a voltage to be applied to a lamp, the reference numeral 37 denotes another selector switch which is arranged on the stand 34 and used for varying sucking force of the pump 35 by selecting a voltage to be applied to said pump, the reference numeral 38 represents a hollow pole planted on the stand 34, the reference numeral 39 designates a hollow arm which is attached to the pole 38 for sustaining the microscope body 4, the reference numeral 40 represents an elastic suction tube which has an end connected to the diaphragm pump 35, extends along the pole 38 and the arm 39, and has an open end in the vicinity of a connector 41 arranged on the arm 39, and the reference numeral 42 designates a light guide which has an end of light incidence facing a light source provided in the stand 34, extends like the suction pipe 40 along the pole 38 and the arm 39, and an end of light emergence attached to the microscope body 4. In addition, the suction tube 40 and the light guide 42 are protected with bushes respectively at the outlet sections from the stand 43, and fixed together to the pole 38 and the arm 39 with cable clamps at adequate intervals. FIG. 6 shows connections from the diaphragm pump 35 through the selector switch 36 to a DC power supply means 43. As is seen from this diagram, both selector switches 36 and 37 are so designed as to allow higher voltages to be applied at the positions indicated by large numerals and turn off the power source means at the "0" positions. Further, electric powers and signals are supplied from the stand 43 to the microscope body 4 through a cable (not shown) which passes through the pole 38 and the arm 39, and is connected to the microscope body by way of a connector 41. The drape 21 is set, in the procedures similar to those described with reference to the Embodiment 1, so as to envelop a portion of the pole 38, the arm 39 and the microscope body 4, thereby maintaining these members and the surroundings thereof in a sterilized condition.

When the selector switch is set, for example, at the "1" position in the Embodiment 2 having the configuration described above, a DC voltage of 4 V is applied to the diaphragm pump 35 to place the pump in the operating condition, whereby air is sucked from inside the drape 21 through the suction tube 40 and exhausted outside. Since the unique open end 23 of the drape 21 is closed with the string 26 fastened to the pole 38, the interior of the drape 21 is kept in a nearly airtight condition. As the internal air is exhausted by the operation of the diaphragm pump 35, internal pressure of the drape 21 is lowered, thereby deflating the drape 21. The deflation of the drape 21 stops when the air suction rate through the slight gaps remaining in the open end 23 bound by the string 26 becomes equal to the flow rate of air exhausted by the diaphragm pump 35. When the selector switch is set at the "2" or "3" position, a higher voltage of 5 V or 6 V is applied to the diaphragm pump 35 and the drape 21 is deflated more tightly. Since the Embodiment 2 permits selecting a weak sucking force to deflate the drape 21 at a low degree when the microscope body 4 and the arm 39 are to be moved for surgical operation or a high sucking force to bring the drape 21 into close contact with the microscope body 4 and the arm 39 when these members are to be fixed during a surgical operation, the use of the drape 21 cannot degrade operability of the operating microscope. As is clear the foregoing description, the open end of the suction tube 40 is used as a suction port, whereby the suction tube 40 and the diaphragm pump 35 constitute an exhaust means.

Figure 7:
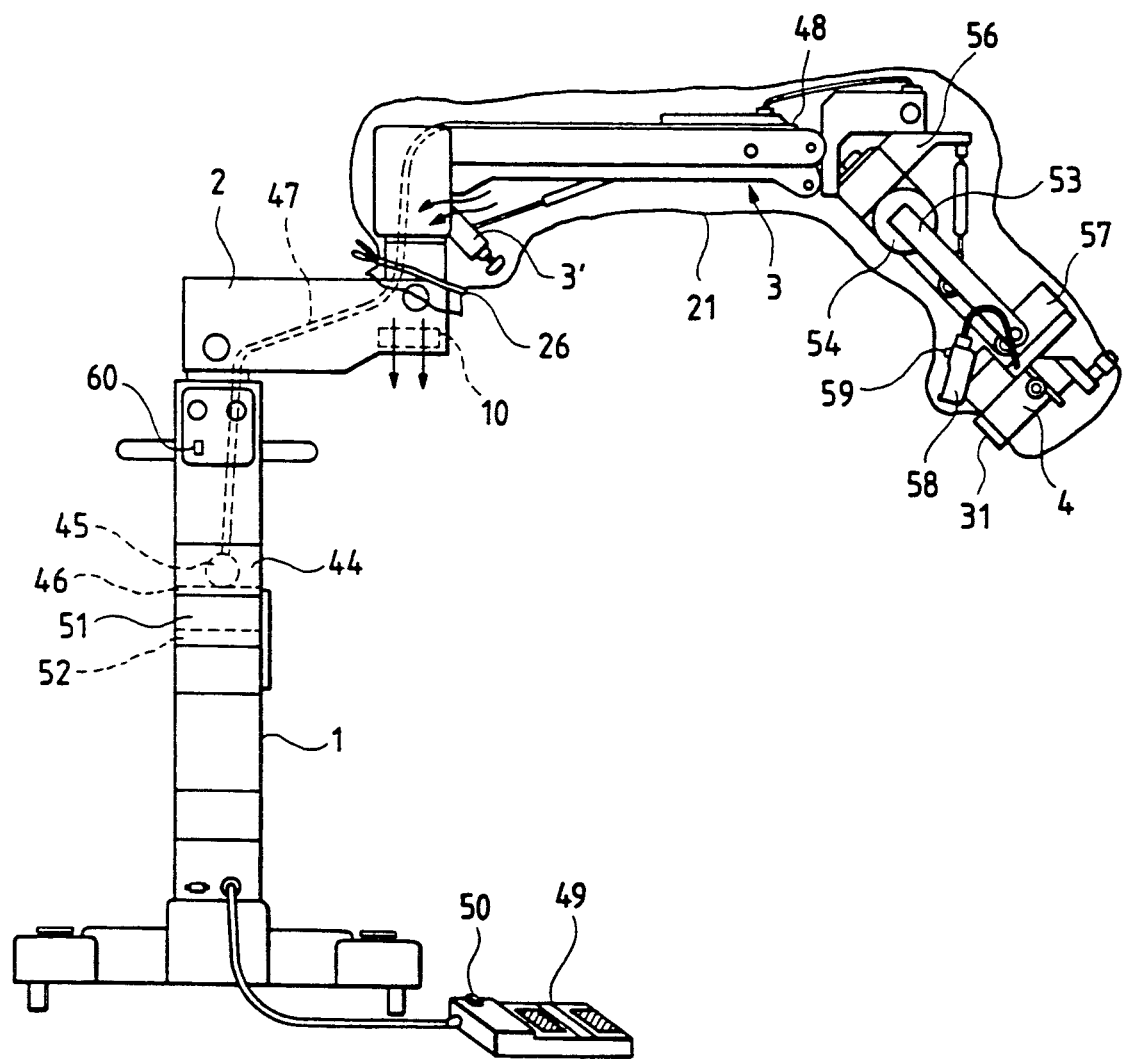
FIG. 7 is a side view illustrating an overall profile of an Embodiment 3 of the operating microscope according to the present invention in a condition where it uses the drape shown in FIG. 3.
Figure 8:
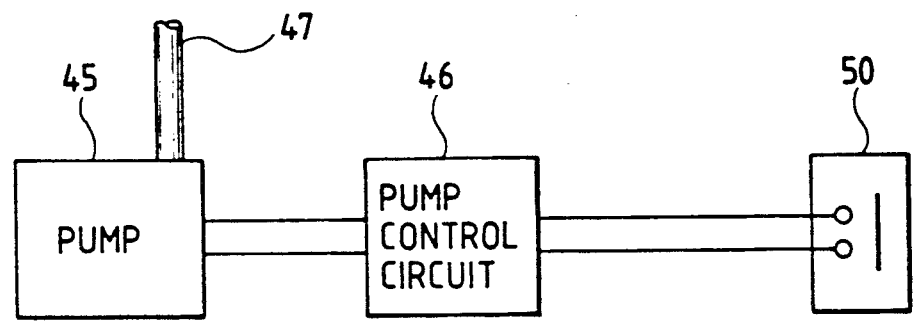
FIG. 8 is a diagram illustrating a pump control circuit to be used in the Embodiment 3 shown in FIG. 7.
Figure 9:
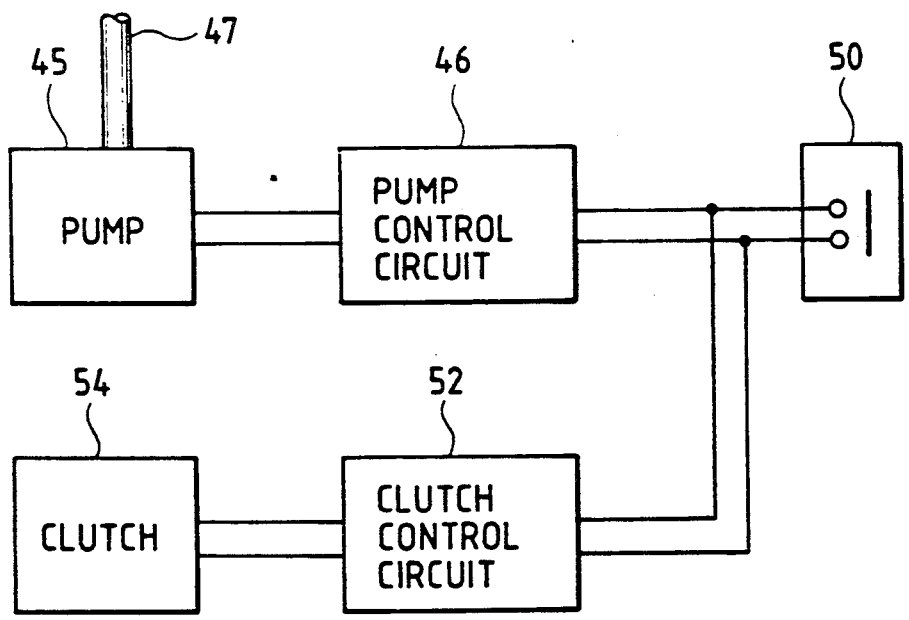
FIG. 9 is a diagram illustrating another pump control circuit which is also to be used in the Embodiment 3 shown in FIG. 7, and consisting of the circuit shown in FIG. 8 and an additional circuit.

FIG. 7 and FIG. 8 illustrate the Embodiment 3 of the present invention. In these drawings, the members and the parts which are the same as those used in the Embodiment 1 will be represented by the same reference numerals. The reference numeral 44 designates a pump unit which is built in the stand 1, and comprises a pump 45 and pump control circuit 46. The reference numeral 47 denotes an elastic air supply tube which has an end 44 connected to the pump 45, extends through the stand 1 and the light source arm 2, and has an open end fixed to the outside of the microscope body support arm 3 at the middle section thereof and serving as an air supply port 46. The reference numeral 49 represents a foot switch unit connected to the stand 1, and the reference numeral 50 designates an operating switch arranged on the foot switch unit 49 and connected to the pump control circuit 46 through the stand 1. FIG. 8 shows connctions from the pump 45 through the pump control circuit 46 to the operating switch 50. By turning on or off the operating switch 50, the pump 45 is placed in operating condition or stopped condition through the pump control circuit 46. The reference numeral 51 denotes a clutch unit which is built in the stand 1 and comprises a clutch control circuit 52. The reference numeral 53 represents a clutch arm which is provided as a component of the microscope body support arm, has an end pivoted to a microscope body suspender 56 by way of a clutch 54 and another end pivoted to a focusing means 57. The reference numeral 58 designates a hand grip fixed to the focusing means 57, and the reference numeral 59 denotes a clutch switch arranged on the hand grip 58. The clutch switch 59 is connected to the clutch 54 through the clutch control circuit 52 so that the clutch 54 is disengaged or engaged through the clutch control circuit 52 by turning on or off the clutch switch 59. In addition, the reference numeral 60 represents a power source switch arranged on the stand 1.

When the operating microscope is enveloped in the drape 21 and then the fan 10 is rotated in the Embodiment 3 having the configuration described above, air pressure is lowered in the drape 21, thereby deflating the drape 21 and bringing it into close contact with the microscope body 4 and the arm 3. Accordingly, the drape 21 which is deflated and fixed with the string does not constitute a hindrance in the visual field nor degrade operability of the operating microscope in the Embodiment 3 as in the case of the Embodiment 1.

By the way, a surgeon often maintains the microscope body 4 at an elevated angle by grasping the hand grip 58, turning on the clutch switch 59 to disengage the clutch 54, turning the clutch arm 53 to set microscope body 4 at an elevated angle and turning off the clutch switch 59 at an adequate position of the micriscope body 4 to engage the clutch 54. These operations for maintaining the microscope body 4 at an elevated angle may be hindered by the drape 21 when it is kept in too close contact with the microscope body 4. These operations can be facilitated by the procedures described below. First, the operating switch 50 is turned on. Then, the pump 45 operates to supply air into the drape 21 through the air supply tube 48 and the drape 21 is swollen so that the clutch arm 53 and the microscope body 4 are movable easily. In addition, it is possible to enhance operability of the operating microscope or supply air into the drape 21 each time the microscope body 4 is to be maintained at an elevated angle by composing the circuit so that the operating switch 50 is usable commonly to the pump control circuit 46 and the clutch control circuit 52. The operating switch 50 can be, needless to say, arranged on the hand grip 58.

Though each of the Embodiments 1 through 3 described above is adapted in such a manner that the suction port 3' formed in the microscope body support arm 3 is used to deflate the drape 21 by exhausting air from the drape, it is possible to exhaust air from the drape through an exhaust port formed in the drape itself.

Figure 10:
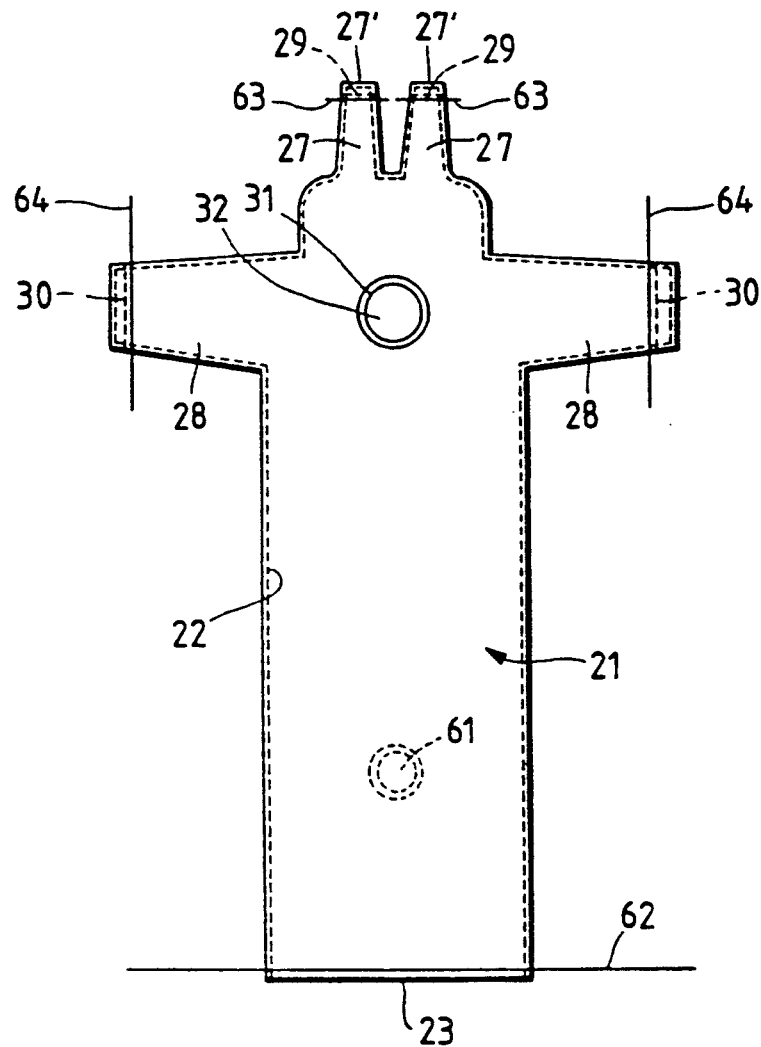
FIG. 10 is a plan view illustrating another example of the drape according to the present invention which is different from the example shown in FIG. 3.
Figure 11:
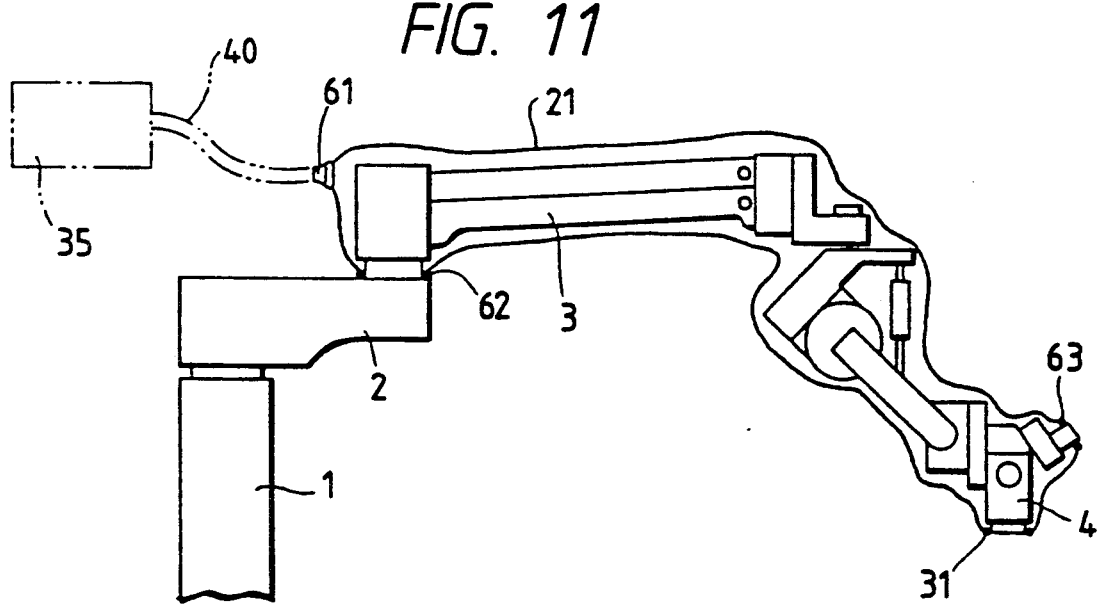
FIG. 11 is a side view illustrating the main parts of the Embodiment 3 of the operating microscope according to the present invention in a condition where it uses the drape shown in FIG. 10.

Various types of drapes having exhaust ports and procedures for uses thereof will be described below. FIG. 10 and FIG. 11 illustrate a drape which is similar to that shown in FIG. 3 but has an air exhaust port. The portions of the drape which are substantially the same as those shown in FIG. 3 are represented by the same reference numerals in FIG. 10 and FIG. 11, and will not be described particularly. In these drawings, the reference numeral 61 represents an air exhaust port which is formed in the drape 21 at an adequate location and to be connected to an exhausting means such as the diaphragm pump 35 described above, and the reference numerals 62, 63 and 64 designate strings which are welded to the open end 23, the eyepiece lens accommodating portions 27 and the accessory accommodating portions 28 repectively, and to be used for bringing the open end 23, eyepiece lens accommodating portions 27 and the accessory accommodating portions 28 into close contact with the microscope body support arm 3, eyepiece tubes and accessory respectively.

Now in accordance with FIG. 11, procedures to envelop the operating microscope into the drape 21 will be described. With the drape 21 kept in a condition where the open end 23 thereof is spread, the section ranging from the microscope body 4 through the microscope body support arm 3 to the light source arm 2 is fitted into the drape 21, the eyepiece lens accommodating portions 27, 27 are fitted over the eyepiece tubes, the ends thereof are fixed by binding them with the strings 63, the tips 27', 27' are cut off along the sewed line by pulling them, the objective lens cap 31 is fitted over the objective lens, and finally the open end is bound around the light source arm 2 by using the string 62 for maintaining the required parts in a sterilized condition. The accessory accommodating portions 28, 28 are folded and fixed to the drape 21 with tapes or the similar means at this stage and, when an accessory is to be used with the operating microscope, can be handled in the procedures similar to those for fitting the eyepiece lens accommodating portions. Then, the air exhaust port 61 of the drape 21 is connected to an air sucking machine such as the diaphragm pump 35 through the suction tube 40. By operating the air sucking machine 35 in this condition, air is exhausted outside from the drape 21. Since the interior of the drape 21 is kept in a substantially airtight condition, the internal air pressure is lowered by exhausting air as described above, and the drape 21 is deflated and brought into close contact with the microscope body 4 and the arm 3. Accordingly, the drape 21 will scarcely hinder the visual field neither degrade operability of the operating microscope since only the ends of the drape 21 are fixed to the operating microscope. When the drape 21 is brought into too close contact with the operating microscope, however, it may somewhat degrade operability of the operating microscope. In such a case, optimum operability can be obtained by contolling output of the air sucking machine 35 so as to deflate the drape 21 at an adequate degree.

FIG. 12 and FIG. 13 show another example of the drape 21 having an exhaust port in a used condition thereof. In this example, the strings 62, 63 and 64 shown in FIG. 10 are not used, but ring-shaped rubber bands 65 are used for fixing not only the open end 23, the eyepiece lens accommodating portions 27 and the surroundings thereof but also the intermediate sections to the members of the operating microscope, thereby maintaining these members in an airtight condition. By connecting the air exhaust port 61 to the air sucking machine 35 through the air suction tube 40 and operating the air sucking machine 35 in the same manner as that described with reference to the example shown in FIG. 10, the drape 21 is deflated and brought into close contact with the microscope body 4 and the arm 3.

The example shown in FIG. 12 and FIG. 13 wherein the ring-shaped rubber bands 65 are used for fixing the drape 21 provides advantages that the procedures to fasten the strings are eliminated, and that the rubber bands have elasticity, unlike the strings, and do not degrade operability of the operating microscope.

FIG. 14 illustrates a still another example of the drape 21. This example is composed by bonding, to the inside surface of the drape 21, a suction tube 66 which has branches extending to the vicinities of the eyepiece lens accommodating portions 27, the accessory accommodating portions 28 and the bonded edge 22 located nearly in the middle of the drape 21, and a stem having a tip protruding out of the open end 23, the tips of said branches serving as the suction port 67 and the tip of the stem serving as the air exhaust port 61. By connecting the air exhaust port 61 to the air sucking machine 35 through the suction tube 40 and operating the air sucking machine 35 after enveloping the operating microscope in the drape 21, the drape 21 is deflated and brought into close contact with the microscope body 4 and the arm 3 without using the rubber bands or strings on the middle portion of the drape 21. In this case, however, it is necessary to maintain the interior of the drape 21 in an airtight condition by using the string 62 or the ring-shaped rubber band 65 on the open end 23 and ring-shaped bands (not shown) on the eyepiece lens accommodating portions 27.

Figure 15:
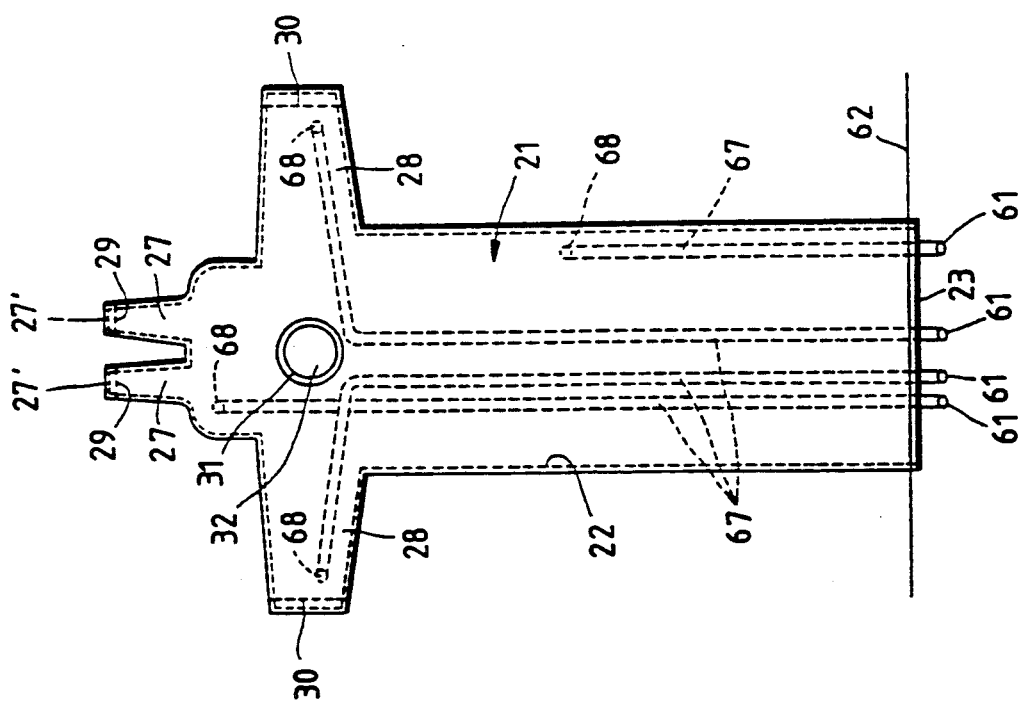

FIG. 15 shows a further example of the drape 21. This example is composed by bonding, to the inside surface of the drape 21, a plurality of suction tubes 67 which have ends extending to the vicinities of the eyepiece lens accommodating portions 27, the accessory accommodating portions 28 and the bonded edge 22 located nearly in the middle of the drape 21, as well as other ends protruding out of the open end 23, said ends serving as suction ports 68 and said other ends serving as the air exhaust ports 61. By connecting the air exhaust ports 61 to a plurality of air sucking machines 35 and operating these machines after enveloping the operating microscope in the drape 21, this example exhibits the effects similar to those of the example shown in FIG. 14. This example permits setting outputs of the individual sucking machines 35 at different levels so as to apply different sucking forces to the portions of the drape 21, thereby making it possible, for example, to adjust sucking forces to certain specific portions of the drape 21 so as not to hinder motions of the movable parts such as rotary members of the operating microscope and bring the other portions into closer contact.

Figure 16:
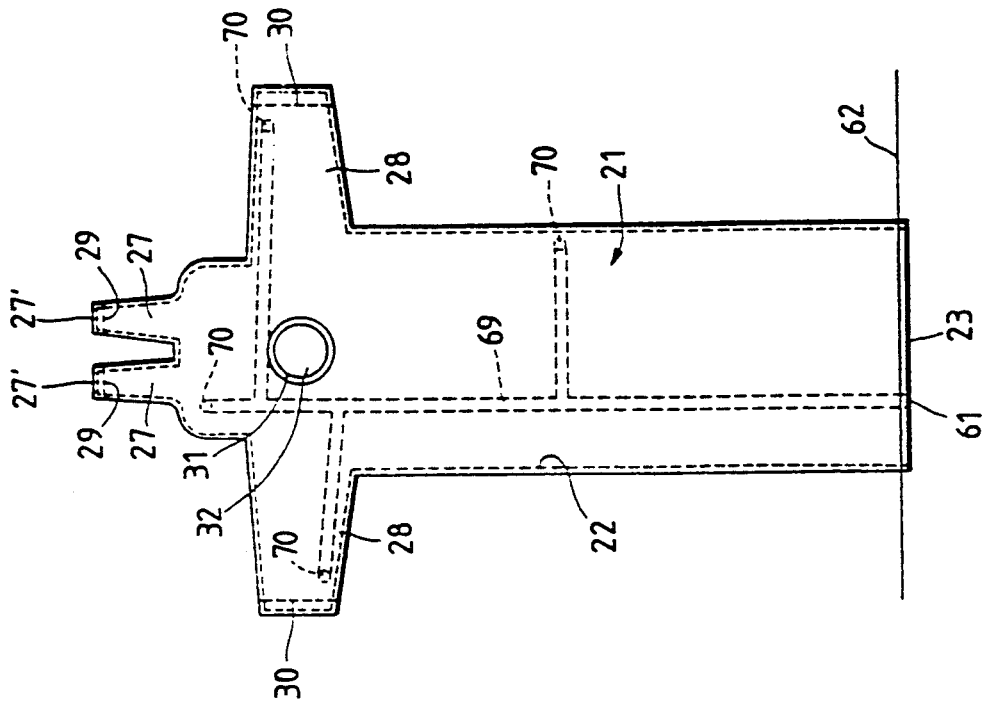

FIG. 16 shows a still further example of the drape 21. In this example, the drape 21 is composed by bonding edges of three clear sheets and bonding two of the three sheets entirely to each other, leaving a branch-shaped pattern so as to form a suction path 69 which corresponds to the suction tube 66 shown in FIG. 14, tips of the branches serving as suction ports 70 and a tip of the stem serving as the air exhaust port 61. Accordingly, this example exhibits the same effects as those of the example shown in FIG. 14 by enveloping the operating microscope in the drape 21, connecting the exhaust port 61 to the air sucking machine 35 and placing the machine in operating condition. Further, this example provides advantages to simplify the manufacturing procedures for the drape 21 and lower manufacturing cost thereof since the drape 21 in this example can be composed only of three clear sheets without using tubes or other component.

What is claimed is:

1. An operating microscope comprising:
   at least one suction port formed in a region to be enveloped in a drape, said suction port being an opening formed in a component member of said microscope; and
   suction means for removing air from said drape and expelling said removed air to air exterior to said drape through said suction port, whereby said drape collapses toward components of said microscope after said air has been removed.

2. An operating microscope according to claim 1, wherein fixtures, including at least one string and at least one ring-shaped rubber band, are attached to said drape for fixing said drape partially to component members of the microscope.

3. An operating microscope according to claim 1, wherein said exhausting means is a fan built in the component member of the microscope.

4. An operating microscope according to claim 1, wherein said suction means is built in the component member of the microscope for adjusting a suction rate, and said suction port is an opening formed in a tip of a suction tube connected to said suction means.

5. An operating microscope comprising a drape covering predetermined portions of the microscope and having at least one air suction port formed therein for removing air from within said drape; and
   suction means disposed external to said drape and connected to said air suction port;
   whereby said suction means create a vacuum within said drape so as to collapse said drape toward component members of said microscope.

6. An operating microscope according to claim 5, wherein said drape includes fixtures, including at least one string and at least one ring-shaped rubber band, attached thereto for partially fixing said drape to a component member of the microscope.

7. An operating microscope according to claim 5 wherein said air suction port is formed as an open end, protruding from said drape, of a suction tube bonded to the inside surface of said drape and having a plurality of suction ports open to the inside of said drape.

8. An operating microscope according to claim 5 wherein said air suction port is composed of open ends, protruding from said drape, of a plurality of suction tubes bonded to the inside surface of said drape and having suction ports open to the inside of said drape.

9. An operating microscope comprising a drape covering predetermined portions of the microscope and having at least one air suction port formed therein for removing air from within said drape, and suction means connected to said air suction port wherein said drape is composed by bonding edges of three clear sheets, and two of the three clear sheets are bonded to each other.

* * * * *